(12) United States Patent
Boyle

(10) Patent No.: US 6,307,078 B1
(45) Date of Patent: Oct. 23, 2001

(54) TRIDENTATE LIGATED HETERONUCLEAR TIN(II) ALKOXIDES FOR USE AS BASE CATALYSTS

(75) Inventor: Timothy J. Boyle, Albuquerque, NM (US)

(73) Assignee: Sandia Corporation, Albuquerque, NM (US)

( * ) Notice: Subject to any disclaimer, the term of this patent is extended or adjusted under 35 U.S.C. 154(b) by 0 days.

(21) Appl. No.: 09/815,869

(22) Filed: Mar. 22, 2001

(51) Int. Cl.[7] ................................ C07F 7/22; C07F 19/00
(52) U.S. Cl. ................................ 556/81; 556/28; 556/12
(58) Field of Search .................... 556/12, 28, 81

(56) References Cited

U.S. PATENT DOCUMENTS

| | | | |
|---|---|---|---|
| 4,496,776 | 1/1985 | Edwards et al. | 568/827 |
| 4,549,017 | 10/1985 | McEntire et al. | 544/168 |
| 4,613,673 | 9/1986 | McEntire et al. | 556/100 |
| 4,675,411 | 6/1987 | Sommer et al. | 546/292 |
| 4,686,315 | 8/1987 | Beach et al. | 585/513 |

*Primary Examiner*—Porfirio Nazario-Gonzalez
(74) *Attorney, Agent, or Firm*—Elmer A. Klavetter

(57) ABSTRACT

Tin alkoxide compounds are provided with accessible electrons. The tin alkoxide compound have the general formula $(THME)_2Sn_3(M(L)_x)_y$, where THME is $(O-CH_2)_3C(CH_3)$, M is a metal atom selected from Sn and Ti, L is an organic/inorganic ligand selected from an alkoxide, a phenoxide or an amide, x is selected from 2 and 4 and y is selected from 0 and 1. These compounds have applicability as base catalysts in reactions and in metal-organic chemical vapor depositions processes.

14 Claims, 5 Drawing Sheets

TRIDENTATE LIGATED HETERONUCLEAR TIN(II) ALKOXIDES FOR USE AS BASE CATALYSTS

This invention was made with Government support under Contract No. DE-AC04-94AL85000 awarded by the Department of Energy. The Government has certain rights in the invention.

BACKGROUND OF THE INVENTION

The present invention relates generally to metal alkoxide compounds and more particularly to a tridentate-ligated tin alkoxides and their method of preparation.

Tin alkoxides are used in applications ranging from electro-active ceramics, conductors, semiconductors, and catalysts. Even though the shape and type of metal cation structures used for metal alkoxide architecture can be well controlled at the atomic-level, metal alkoxides have not been generally used as catalysts. Typically, those metal alkoxides that are used as catalysts involve alkali metal alkoxides. Alkyl aluminum alkoxides have also been used as part of a complex mixture to oligomerize ethylene (U.S. Pat. No. 4,686,315, issued on Aug. 11, 1987). There are also some reports of Group IV metal alkoxide for the production of polyacrylates, polyamides, and allylic alcohols (U.S. Pat. No. 4,496,776, issued on Jan. 29, 1985; U.S. Pat. No. 4,549,017, issued on Oct. 22, 1985). However, in general these materials are used as supports and not necessarily the active site of polymerization.

Sommer et al. (U.S. Pat. No. 4,675,411, issued on Jun. 23, 1987) and McEntire et al. (U.S. Pat. No. 4,613,673, issued on Sep. 23, 1986) using tin alkoxides have been reported; however, these compounds are reacted to form in situ compounds that are not metal alkoxides but metal amides.

The low use of metal alkoxides as catalysts is typically attributed to the large charge/cation size ratio that leads to cluster formation to satisfy the various cation's coordination sphere demands. Because of this hyper-oligomerization, reactive sites on the metal are rendered inaccessible. Even for those metal alkoxides that do not oligomerize, ligand rearrangement results in solution functionality that again can neutralize potential active sites. Thus, metal alkoxides are typically poor catalysts due to hindered reactive sites. This is typically due to the dynamic behavior metal alkoxide compounds exhibit in solution coupled with the large cation to small charge ratio that promotes oligomerization.

Useful would be tin compounds that have available electrons that can be used both in solution and as thin films.

DETAILED DESCRIPTION OF THE INVENTION

Figure 1:
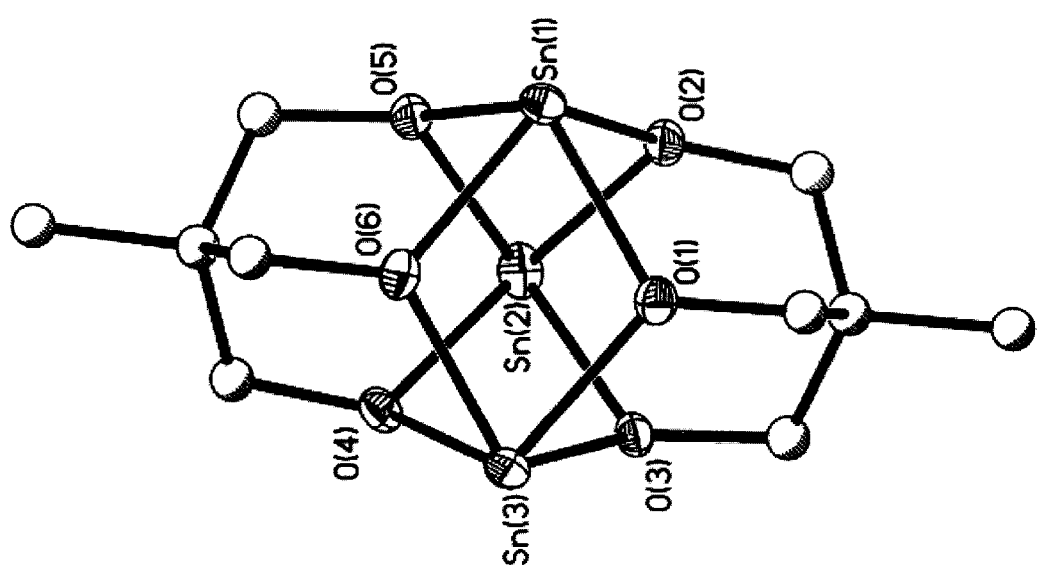
FIG. 1 illustrates the structure of $(THME)_2Sn_3$.

Introduction of multi-dentate ligands can be used to mitigate hindered reactive sites due to ligand rearrangement in metal alkoxides. Using multi-dentate ligands can complex coordination sites as well as mitigate potential dynamic behavior in solution. The present invention provides tin alkoxide compositions that have availability of electrons in the structure of the tin alkoxides utilizing tri-dentate ligands.

Using the tridentate ligand, tris(hydroxymethyl)ethane $(HO\text{---}CH_2)_3C(CH_3)$ (hereinafter referred to as THME-H$_3$) in the present invention, tin (II) alkoxide complexes have been isolated that possess identical tin cation ($Sn^{+2}$) sites that are bound to one another through oxygen atoms. The compound $(O\text{---}CH_2)_3C(CH_3)$ is designated hereinafter as THME. The $Sn^{+2}$ cations are in close proximity to each other due to the tridentate ligand forming a spherical cluster. Thus, a new class of structural tin alkoxides is formed, $(\mu\text{-}THME)_2Sn_3(M(L)_x)_y$, where M is a metal atom selected from Sn and Ti and L is an organic/inorganic ligand, where x is selected from 2 and 4 and y selected from 0 and 1.

The simplest structure formed is when y is 0, yielding $(\mu\text{-}THME)_2Sn_3$, or more simply just $(THME)_2Sn_3$, where the symbol $\mu$ indicates a single bridging ligand between two metal atoms. This arrangement leads to each of the sterochemically active electron pair on each Sn atom to point out from the central core of the molecules. Control of the steric environment and reactive properties of the active site are possible through substitution of the hydrocarbon groups of the alkoxide and synthesis of binuclear complexes and through introduction of additional Sn cations. The subsequent $(\mu\text{-}THME)_2Sn_3$ derivatives allow for increased metal sites and control over steric influences through the introduction of alternative metal alkoxides $(M(L)_x)$. These compounds are similar to $(THME)_2Sn_3$ with the active electron pairs also readily accessible, but additional metal sites are available. The organic/inorganic ligand L can be any alkyl oxide group, including alkoxides with 1 to 5 carbon atoms, such as methoxide $(OCH_3)$, ethoxide $(OCH_2CH_3)$, propoxide $(O(CH_2)_2CH_3)$, iso-propoxide $(OCH(CH_3)_2)$, butoxide $(O(CH_2)_3CH_3)$, tert-butoxide $(OC(CH_3)_3)$, and neopentoxide $(OCH_2C(CH_3)_3)$, aryloxides such as phenoxide and substituted phenoxides such as the 2,6 di-substituted $OC_6H_3(CH_3)_2$, designated as $OC_6H_3(CH_3)_2\text{-}2,6$, and amides such as $N(Si(CH_3)_3)_2$.

The tridentate ligated tin alkoxide compounds of the present invention have been formulated maintaining tin as Sn(II) rather than Sn(IV) to provide structures that have accessible electrons (the Sn lone pair of electrons) and that, unlike other metal alkoxides, do not have dynamic behavior in solution that can neutralize effective active sites. These accessible electrons enable the compounds to be used as base catalysts or as bases in other reactions. The inclusion of additional metals leads increased utility for reduction-oxidation reactions. The compounds can advantageously be used in solution or as thin films. The compounds can also be used as reagents in metal-organic chemical vapor deposition reactions.

In one embodiment of the tridentate ligated tin alkoxide compounds of the present invention, $(THME)_2Sn_3$ has been made having accessible electrons, with a structure illustrated in FIG. 1. In the method of the present invention, the addition of THME-H$_3$ to $Sn(NR_2)_2$ where $NR_2=N(CH_3)_2$, $N(Si(CH_3)_3)_2$ in a non-reactive solve yields the product $(THME)_2Sn_3$.

Figure 2:
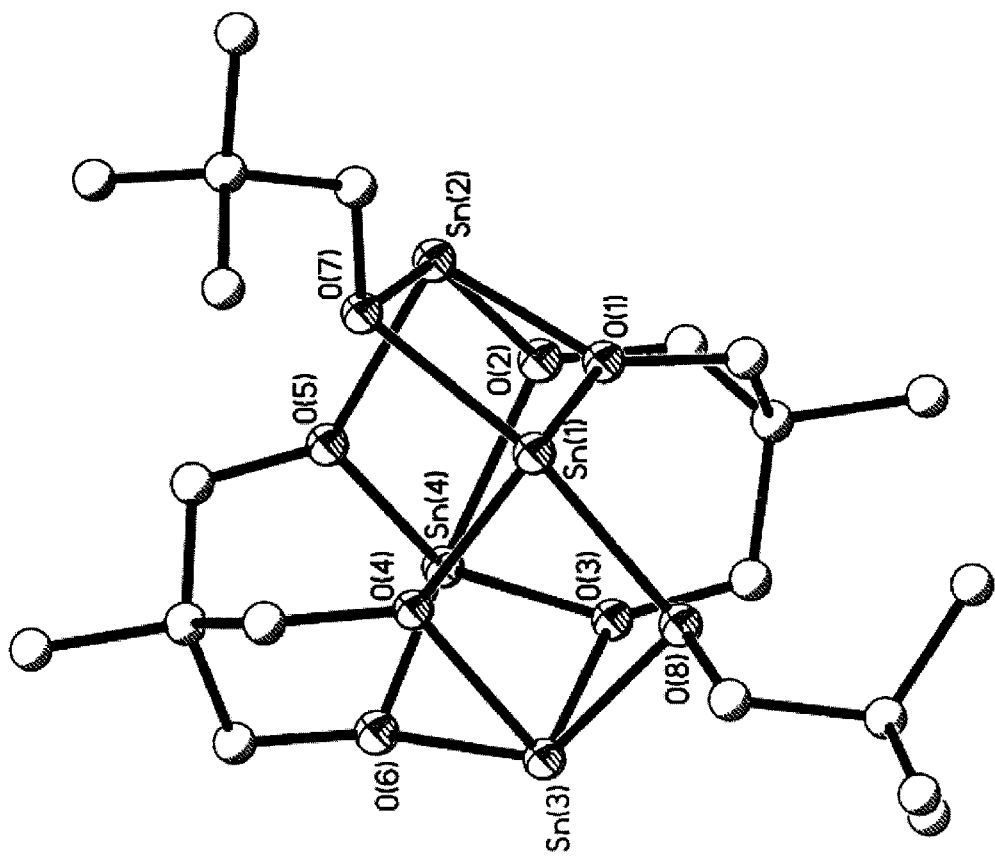
FIG. 2 illustrates the structure of $(THME)_2Sn_4(\mu\text{-}OCH_2C(CH_3)_3)_2$.
Figure 3:
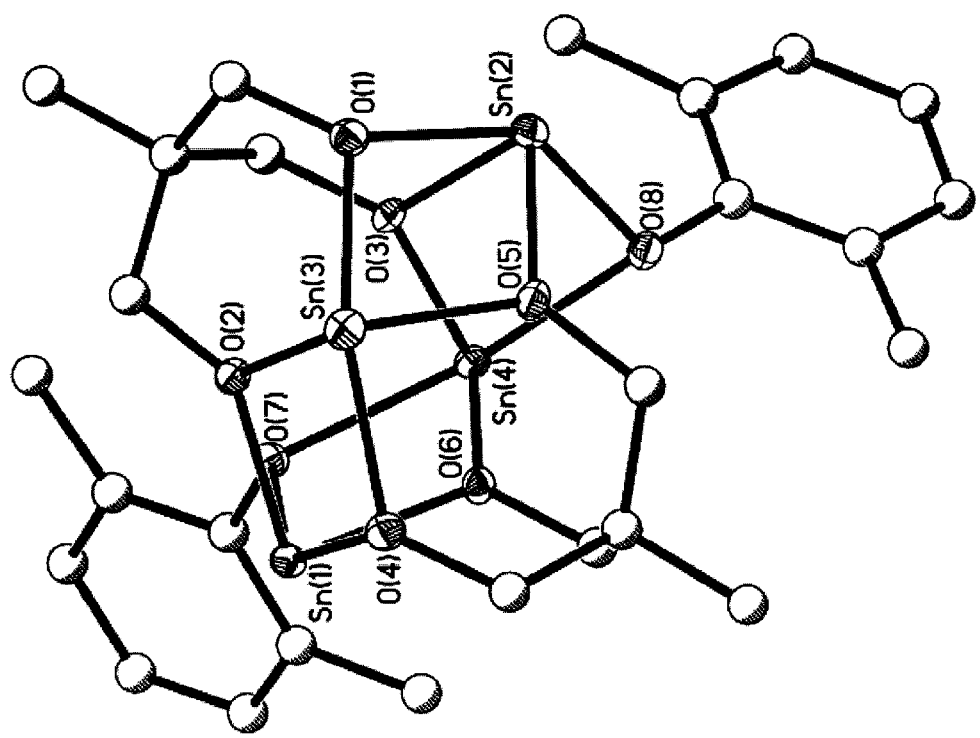
FIG. 3 illustrates the structure of $(THME)_2Sn_4(\mu\text{-}OCH_6H_3(CH_3)_2\text{-}2,6)_2$.
Figure 4:
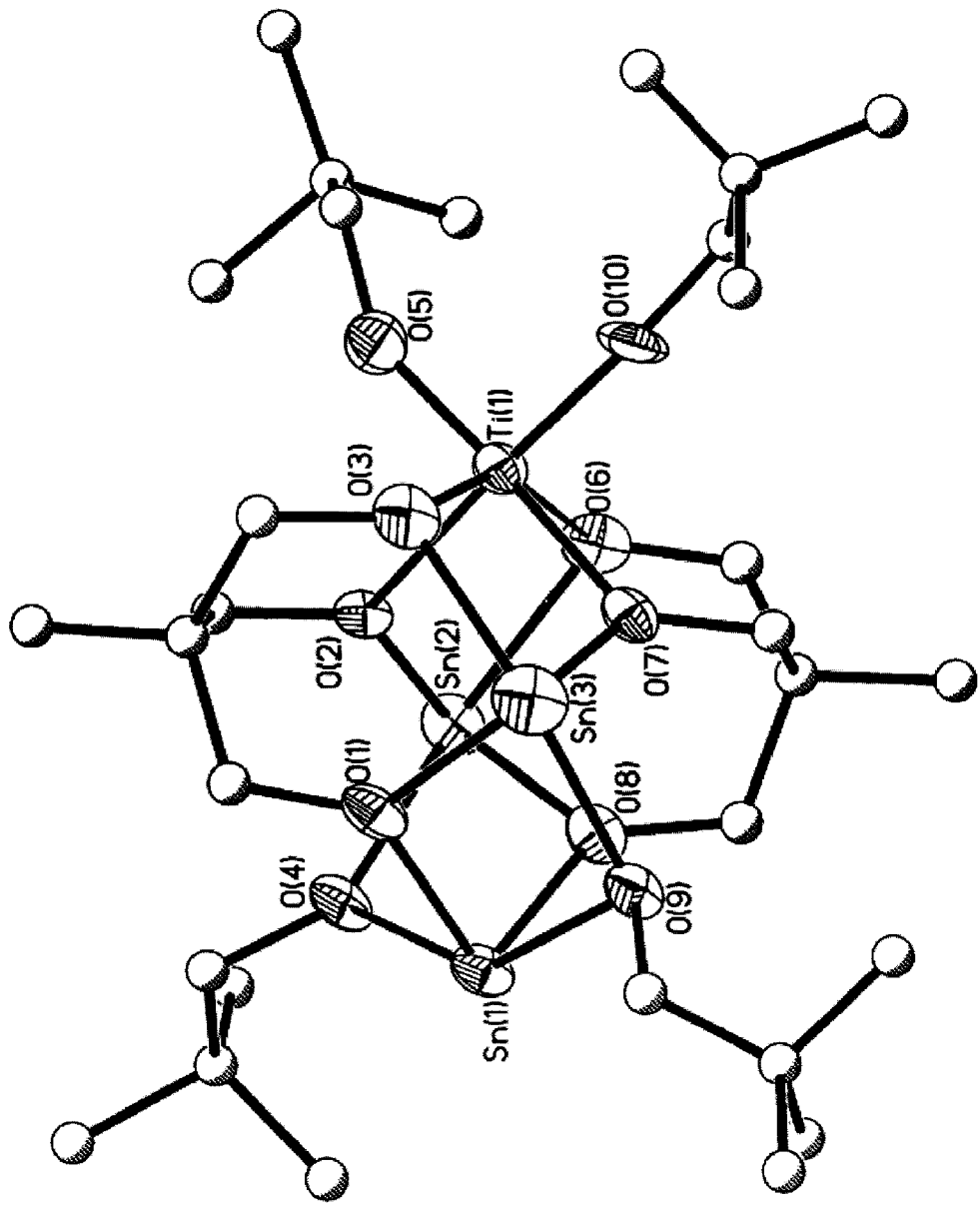
FIG. 4 illustrates the structure of $(THME)_2Sn_3(\mu\text{-}OCH_2C(CH_3)_3)_2Ti(OCH_2C(CH_3)_3)_2$.
Figure 5:
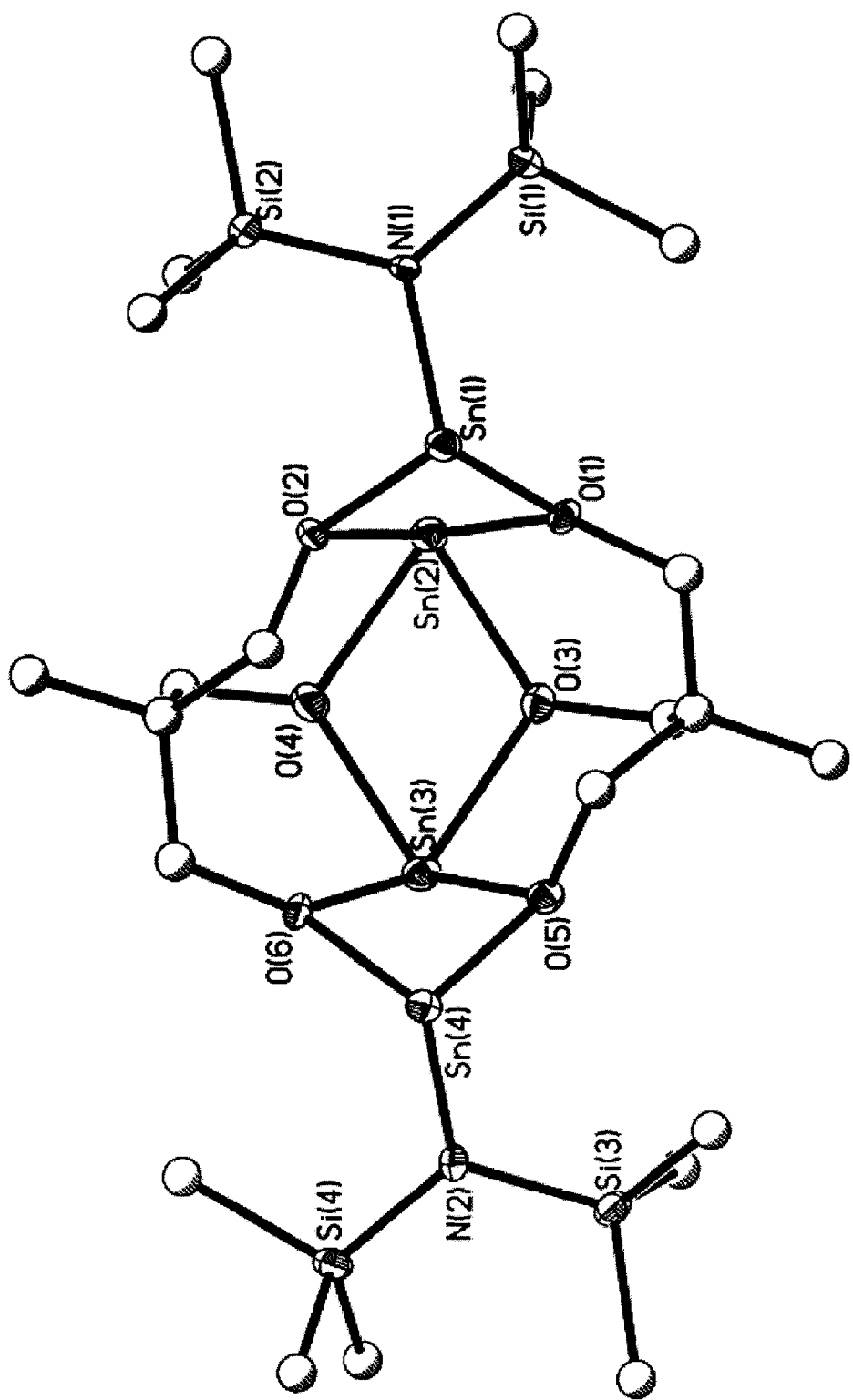
FIG. 5 illustrates the structure of $(THME)_2Sn_4(N(Si(CH_3)_3)_2)_2$.

The structure of $(THME)_2Sn_3$ can be modified by other metal alkoxides by mixing $(THME)_2Sn_3$ with other metal alkoxide or metal phenoxide compounds at room temperature. By addition of other Sn or Ti compounds, a variety of alternative molecules that maintain the structural rigidity can be generated. For instance, using $Sn(OR)_2$, where $OR=OCH_2C(CH_3)_3)_2$ and $\mu\text{-}OC_6H_3(CH_3)_2\text{-}2,6$, the structure enlarged forming $(THME)_2Sn_4(\mu\text{-}OR)_2$. In one embodiment, $(THME)_2Sn_4(\mu\text{-}OCH_2C(CH_3)_3)_2$ is formed, with the structure illustrated in FIG. 2. FIG. 3 illustrates the structure of another embodiment, $(THME)_2Sn_4(\mu\text{-}OC_6H_3(CH_3)_2\text{-}2,6)_2$, where this compound has a phenoxide ligand. FIG. 4 illustrates the structure of yet another embodiment, $(THME)_2Sn_3(\mu\text{-}OCH_2C(CH_3)_3)_2Ti(OCH_2C(CH_3)_3)_2$, which can be alternatively written as $(THME)_2Sn_3Ti(OCH_2C(CH_3)_3)_4$. FIG. 5 illustrates the structure of yet another embodiment, $(THME)_2Sn_4(N(Si(CH_3)_3)_2)_2$.

NMR (nuclear magnetic resonance) analysis for as-prepared compounds of the present invention yield spectra with a solution (THF-$d_5$) $^{119}$Sn peaks at −330 ppm for $(THME)_2Sn_3$, −324,−358,−372 ppm for $(THME)_2Sn_4(\mu\text{-}OCH_2C(CH_3)_3)_2$, −391, −359 ppm for $(THME)_2Sn_4(\mu\text{-}OC_6H_3(CH_3)_2\text{-}2,6)_2$, −358 (1 Sn), −403 (2 Sn) ppm for $(THME)_2Sn_3Ti(OCH_2C(CH_3)_3)_4$, and −452 for $(THME)_2Sn_4(N(Si(CH_3)_3)_2)_2$.

Table 1 shows the crystal data and structure refinement for $(THME)_2Sn_3$. This is one example of numerous crystal structure solutions for this molecule. The dimensions of the unit cell and the number of molecules per unit cell are due to diverse packing nature of $(THME)_2Sn_3$. Further, solvent inclusion in the lattice has led to additional variations in the parameters noted for $(THME)_2Sn_3$. Table 2 shows the crystal data and structure refinement for $(THME)_2Sn_4(\mu\text{-}OCH_2C(CH_3)_3)_2$. Table 3 shows the crystal data and structure refinement for $(THME)_2Sn_4(\mu\text{-}OC_6H_3(CH_3)_2\text{-}2,6)_2$. Table 4 shows the crystal data and structure refinement for $(THME)_2Sn_3Ti(OCH_2C(CH_3)_3)_4$. Table 5 shows the crystal data and structure refinement for $(THME)_2Sn_4(N(Si(CH_3)_3)_2)_2$. The temperature used was 168 K. The refinement method was a full-matrix least-squares on $F^2$. The data was corrected for absorption using the program SADABS. Tables 6, 7, 8, 9, and 10 give the atomic coordinates and equivalent isotropic displacement parameters ($Å^2 \times 10^3$) for the structures of $(THME)_2Sn_3$, $(THME)_2Sn_4(\mu\text{-}OCH_2C(CH_3)_3)_2$, $(THME)_2Sn_4(\mu\text{-}OC_6H_3(CH_3)_2\text{-}2,6)_2$, $(THME)_2Sn_3Ti(OCH_2C(CH_3)_3)_4$, and $(THME)_2Sn_4(N(Si(CH_3)_3)_2)_2$, respectively. U(eq) is defined as one third of the trace of the orthogonalized $U_{ij}$ tensor.

TABLE 1

Crystal data and structure refinement for $[Sn_3(THME)_2]_2$. There are two molecules per unit cell

| | |
|---|---|
| Empirical formula | C26 H55 O12 N Si2 Sn6 |
| Formula weight | 1341.83 |
| Temperature | 168(2)K |
| Wavelength | 0.71073 Å |
| Crystal system, space group | Orthorhombic, Pbca |
| Unit cell dimensions | | a = 12.3874(7) Å alpha = 90 deg.
b = 22.6507(13) Å beta = 90 deg.
c = 25.3335(15) Å gamma = 90 deg.

| | |
|---|---|
| Z, Calculated density | 8, 2.509 Mg/m³ |
| Absorption coefficient | 4.307 mm⁻¹ |
| F(000) | 4726 |
| Theta range for data collection | 1.61 to 28.28 deg. |
| Limiting indices | −15<=h<=15, −29<=k<=13, −33<=l<=32 |
| Reflections collected/unique | 43229/8484 [R(int) = 0.0449] |
| Data / restraints / parameters | 8484 / 0 / 347 |
| Goodness-of-fit on F² | 0.923 |

TABLE 1-continued

Crystal data and structure refinement for $[Sn_3(THME)_2]_2$. There are two molecules per unit cell

| | |
|---|---|
| Final R indices [I>2sigma(I)] | R1 = 0.0248, wR2 = 0.0464 |
| R indices (all data) | R1 = 0.0453, wR2 = 0.0510 |

TABLE 2

Crystal data and structure refinement for $(THME)_2Sn_4(OCH_2C(CH_3)_3)_2$.

| | |
|---|---|
| Empirical formula | C20 H40 O8 Sn4 |
| Formula weight | 883.28 |
| Temperature | 168(2)K |
| Wavelength | 0.71073 Å |
| Crystal system, space group | Triclinic, P-1 |
| Unit cell dimensions | | a = 11.0984(16) Å alpha = 109.963(2) deg.
b = 11.9361(17) Å beta = 100.248(2) deg.
c = 12.1199(17) Å gamma = 99.461(2) deg.

| | |
|---|---|
| Z, Calculated density | 2, 2.037 Mg/m³ |
| Absorption coefficient | 3.465 mm⁻¹ |
| F(000) | 848 |
| Theta range for data collection | 1.85 to 28.27 deg. |
| Limiting indices | −14<=h<=12, −15<=k<=15, −14<=l<=16 |
| Reflections collected / unique | 9078 / 6323 [R(int) = 0.0201] |
| Data / restraints / parameters | 6323 / 0 / 297 |
| Goodness-of-fit on F² | 1.040 |
| Final R indices [I>2sigma(I)] | R1 = 0.0319, wR2 = 0.0812 |
| R indices (all data) | R1 = 0.0437, wR2 = 0.0886 |

TABLE 3

Crystal data and structure refinement for $(THME)_2Sn_4(OC_6H_3(CH_3)_2\text{-}2,6)_2$.

| | |
|---|---|
| Empirical formula | C26 H36 O8 Sn4 |
| Formula weight | 951.31 |
| Crystal system, space group | Monoclinic, P2(1)/c |
| Unit cell dimensions | | a = 19.4460(14) Å alpha = 90 deg.
b = 8.3861(6) Å beta = 92.6900(10) deg.
c = 18.4826(13) Å gamma = 90 deg

| | |
|---|---|
| Z, Calculated density | 4, 2.099 Mg/m³ |
| Absorption coefficient | 3.324 mm⁻¹ |
| F(000) | 1824 |
| Theta range for data collection | 2.21 to 28.28 deg. |
| Limiting indices | −23<=h<=25, −10<=k<=11, −23<=l<=24 |
| Reflections collected/unique | 18764/7081 [R(int) = 0.0498] |
| Completeness to theta = 28.28 | 94.7% |
| Data / restraints / parameters | 7081 / 0 / 349 |
| Goodness-of-fit on F² | 0.890 |
| Final R indices [I>2sigma(I)] | R1 = 0.0331, wR2 = 0.0576 |
| R indices (all data) | R1 = 0.0681, wR2 = 0.0647 |

TABLE 4

Crystal data and structure refinement for $(THME)_2Sn_3(OCH_2C(CH_3)_3)_2Ti(OCH_2C(CH_3)_3)_2$.

| | |
|---|---|
| Empirical formula | C30 H62 O10 Sn3 Ti |
| Formula weight | 986.77 |
| Temperature | 168(2)K |
| Wavelength | 0.71073 Å |
| Crystal system, space group | Monoclinic, P2(1)/c |

TABLE 4-continued

Crystal data and structure refinement for
$(THME)_2Sn_3(OCH_2C(CH_3)_3)_2Ti(OCH_2C(CH_3)_3)_2$.

Unit cell dimensions a = 17.174(10) Å alpha = 90 deg.
b = 18.681(11) Å beta = 106.920(10) deg.
c = 13.090(7) Å gamma = 90 deg.

| | |
|---|---|
| Z, Calculated density | 4, 1.631 Mg/m³ |
| Absorption coefficient | 2.081 mm⁻¹ |
| F(000) | 1976 |
| Theta range for data collection | 1.65 to 23.33 deg. |
| Limiting indices | −19<=h<=18, −20<=k<=18, −11<=l<=14 |
| Reflections collected/unique | 17500/5802 [R(int) = 0.1711] |
| Completeness to theta = 23.33 | 99.5% |
| Data / restraints / parameters | 5802 / 0 / 411 |
| Goodness-of-fit on F² | 0.849 |
| Final R indices [I>2sigma(I)] | R1 = 0.0725, wR2 = 0.1276 |
| R indices (all data) | R1 = 0.1998, wR2 = 0.1587 |

TABLE 5

Crystal data and structure refinement for $(THME)_2Sn_4(N(Si(CH_3)_3)_2)_2$.

| | |
|---|---|
| Empirical formula | C22 H54 N2 O6 Si4 Sn4 |
| Formula weight | 1029.79 |
| Wavelength | 0.71073 Å |
| Crystal system, space group | Monoclinic, P2(1) |

Unit cell dimensions a = 6.834(3) Å alpha = 90 deg.
b = 17.680(7) Å beta = 101.050(5) deg.
c = 15.981(6) Å gamma = 90 deg.

| | |
|---|---|
| Z, Calculated density | 2, 1.805 Mg/m³ |
| Absorption coefficient | 2.765 mm⁻¹ |
| F(000) | 1008 |
| Theta range for data collection | 1.30 to 23.27 deg. |
| Limiting indices | −5<=h<=7, −19<=k<=19, −16<=l<=17 |
| Reflections collected/unique | 8981/5324 [R(int) = 0.0347] |
| Completeness to theta = 23.27 | 99.8% |
| Data / restraints / parameters | 5324 / 1 / 357 |
| Goodness-of-fit on F | 1.002 |
| Final R indices [I>2sigma(I)] | R1 = 0.0395, wR2 = 0.0890 |
| R indices (all data) | R1 = 0.0449, wR2 = 0.0921 |

Metals other than tin in these compounds, such as lead, were investigated but do not produce structures with accessible electrons similar to the THME ligated species. This is considered to be partially the result of the size and charge of the tin atoms. The large size to small cation ratio allows for the arrangement to be observed. For other systems, the cation have too great a charge or the charge is variable, or the size of the cation is inappropriate.

In one embodiment, the $(THME)_2Sn_3$ is formulated by dissolving a precursor tin compound, such as $(Sn(N(CH_3)_2)_2)_2$ in a non-reactive solvent (that is, a solvent which does not react with the precursor tin compound or subsequent tin alkoxide compounds), where the solvent can be any polar or non-polar organic solvent in which the precursor compound is soluble. Such solvents include, but are not limited to alkanes, alkyl organic solvents, aryl organic solvents, and polar solvents. Examples of these solvents would include hexanes, toluene, tetrahydrofuran (THF), and pyridine. Alcohols and ketones should not be used as these solvents react with metal alkoxides. The volatile material of the reaction can be removed in vacuo to produce a white powder which was identified as $(THME)_2Sn_3$.

In one embodiment to make one alkoxide-modified product of $(THME)_2Sn_3$, $(THME)_2Sn_3$ is first dissolved in a suitable non-reactive polar or non-polar organic solvent. Approximately one equivalent of the appropriate metal alkoxide was added and the solution, stirred, warmed, concentrated, and allowed to set to produce crystals of $(THME)_2Sn_4(OR)_2$ and $(THME)_2Sn_3(\mu\text{-}ONep)_2Ti(ONep)_2$. As seen in FIGS. 3–5, these modified products contain THME tridentate ligands and an additional metal alkoxide.

Formation of an amide modified $(THME)_2Sn_2$ was undertaken in a similar manner. $(THME)_2Sn_3$ was dissolved in THF with $Sn(N(Si(CH_3)_3)_2)_2$ The reaction was heated to boiling and allowed to cool to room temperature. Another route was to dissolve two equivalents of THME-$H_3$ with four equivalents of $Sn(N(Si(CH_3)_3)_2)_2$ in THF and heated; the reaction was allowed to cool to room temperature. FIG. 5 illustrates the modified product.

Once the crystals were formed, typically by slow evaporation, single crystal X-ray diffraction experiments were undertaken to determine structure and other characteristics. All crystals were mounted onto a thin glass fiber and immediately placed under a liquid $N_2$ stream, on a Bruker AXS diffractometer. The radiation used was graphite monochromatized MoKα radiation ($\lambda$=0.71073 Å). The lattice parameters were optimized from a least-squares calculation on 58 carefully centered reflections. Lattice determination, data collection, data reduction, structure solution, and structure refinement was performed and the data corrected for absorption. Each structure was solved using direct methods that yielded the heavier atoms, along with a number of the C atoms. Subsequent Fourier synthesis yielded the remaining C atom positions. The hydrogen atoms were fixed in positions of ideal geometry and refined. These idealized hydrogen atoms had their isotropic temperature factors fixed at 1.2 or 1.5 times the equivalent isotropic U of the C atoms they were bonded to. The final refinement of each compound included anisotropic thermal parameters on all non-hydrogen atoms.

TABLE 6

Atomic coordinates (x 10⁴) and equivalent isotropic displacement parameters (Å² x 10³) for $[Sn_3(THME)_2]_2$.

| | x | y | z | U (eq) |
|---|---|---|---|---|
| Sn(1) | 3724(1) | 984(1) | 6830(1) | 31(1) |
| Sn(2) | 6139(1) | 1707(1) | 6558(1) | 31(1) |
| Sn(3) | 6090(1) | 534(1) | 7443(1) | 30(1) |
| Sn(4) | 3682(1) | 1479(1) | −246(1) | 33(1) |
| Sn(5) | 1686(1) | 1505(1) | 711(1) | 35(1) |
| Sn(6) | 4282(1) | 1967(1) | 1024(1) | 37(1) |
| O(1) | 4817(2) | 232(1) | 6897(1) | 31(1) |
| O(2) | 4872(2) | 1178(1) | 6183(1) | 32(1) |
| O(3) | 6752(2) | 813(1) | 6684(1) | 30(1) |
| O(4) | 6429(2) | 1491(1) | 7400(1) | 30(1) |
| O(5) | 4520(2) | 1840(1) | 6903(1) | 30(1) |
| O(6) | 4487(2) | 907(1) | 7609(1) | 29(1) |
| O(7) | 2607(2) | 2279(1) | 961(1) | 35(1) |
| O(8) | 2137(2) | 1884(1) | −53(1) | 31(1) |
| O(9) | 4215(2) | 2262(1) | 194(1) | 35(1) |
| O(10) | 4665(2) | 1274(1) | 442(1) | 33(1) |
| O(11) | 3067(2) | 1285(1) | 1213(1) | 34(1) |
| O(12) | 2596(2) | 888(1) | 202(1) | 32(1) |
| C(1) | 5075(3) | −113(2) | 6443(1) | 36(1) |
| C(2) | 5758(3) | 205(2) | 6029(1) | 32(1) |
| C(3) | 5142(3) | 733(2) | 5804(1) | 38(1) |
| C(4) | 5974(3) | −227(2) | 5577(1) | 47(1) |
| C(5) | 6083(3) | 1887(2) | 7806(1) | 38(1) |
| C(6) | 4354(3) | 1355(2) | 8002(1) | 34(1) |
| C(7) | 4362(3) | 2195(2) | 7358(1) | 36(1) |
| C(8) | 3832(3) | 2838(2) | 61(2) | 38(1) |
| C(9) | 2628(3) | 2925(2) | 161(1) | 32(1) |
| C(10) | 1963(3) | 2496(2) | −167(1) | 38(1) |

TABLE 6-continued

Atomic coordinates (× 10⁴) and equivalent isotropic
displacement parameters (Å² × 10³) for [Sn₃(THME)₂]₂.

|  | x | y | z | U (eq) |
|---|---|---|---|---|
| C(11) | 2317(3) | 3553(2) | 2(2) | 44(1) |
| C(12) | 2971(3) | 333(2) | 390(1) | 37(1) |
| C(13) | 3834(3) | 371(2) | 822(1) | 33(1) |
| C(14) | 4846(3) | 682(2) | 614(1) | 36(1) |
| C(15) | 4863(3) | 1944(2) | 7863(1) | 31(1) |
| C(16) | 4633(3) | 2379(2) | 8318(1) | 44(1) |
| C(17) | 6841(3) | 402(2) | 6258(1) | 36(1) |
| C(18) | 2377(3) | 2850(2) | 751(1) | 40(1) |
| C(19) | 3385(3) | 689(2) | 1307(1) | 39(1) |
| C(20) | 4152(3) | −255(2) | 984(1) | 44(1) |

TABLE 7

Atomic coordinates (× 10⁴) and equivalent isotropic displacement
parameters (Åˢ × 10³) for (THME)₂Sn₄(μ-OCH₂C(CH₃)₃)₂.

|  | x | y | z | U (eq) |
|---|---|---|---|---|
| Sn(1) | 7511(1) | 1245(1) | 4608(1) | 30(1) |
| Sn(2) | 7698(1) | 4193(1) | 4483(1) | 31(1) |
| Sn(3) | 5445(1) | −103(1) | 1665(1) | 30(1) |
| Sn(4) | 5620(1) | 2858(1) | 1536(1) | 30(1) |
| O(1) | 8301(2) | 2510(3) | 3888(2) | 31(1) |
| O(2) | 7567(3) | 3911(2) | 2580(3) | 33(1) |
| O(3) | 6545(2) | 1381(2) | 1401(2) | 27(1) |
| O(4) | 5633(2) | 921(2) | 3572(2) | 28(1) |
| O(5) | 5780(2) | 3429(2) | 3465(2) | 29(1) |
| O(6) | 4317(3) | 1253(3) | 1551(2) | 33(1) |
| O(7) | 7156(2) | 3100(2) | 5609(2) | 30(1) |
| O(8) | 7325(3) | −139(2) | 2727(3) | 34(1) |
| C(1) | 9207(4) | 2313(4) | 3171(4) | 36(1) |
| C(2) | 8586(4) | 3656(4) | 2065(4) | 38(1) |
| C(3) | 7698(4) | 1362(4) | 1049(4) | 33(1) |
| C(4) | 8830(4) | 2399(4) | 1939(4) | 32(1) |
| C(5) | 9954(4) | 2255(5) | 1367(5) | 47(1) |
| C(6) | 4593(4) | 1212(4) | 4058(4) | 31(1) |
| C(7) | 4721(4) | 3332(4) | 3978(4) | 30(1) |
| C(8) | 3380(4) | 1430(4) | 2199(4) | 40(1) |
| C(9) | 3899(4) | 2024(4) | 3581(4) | 31(1) |
| C(10) | 2788(4) | 2148(4) | 4159(4) | 41(1) |
| C(11) | 7974(4) | 3678(4) | 6796(4) | 39(1) |
| C(12) | 7323(4) | 3775(4) | 7818(4) | 33(1) |
| C(13) | 6744(6) | 2503(5) | 7752(5) | 61(2) |
| C(14) | 8360(5) | 4433(4) | 9013(4) | 51(1) |
| C(15) | 6336(6) | 4497(6) | 7768(5) | 70(2) |
| C(16) | 7331(6) | −1323(4) | 2760(5) | 59(2) |
| C(17) | 8249(4) | −1948(4) | 2154(5) | 44(1) |
| C(18) | 7863(8) | −2236(6) | 836(6) | 92(3) |
| C(19) | 9557(6) | −1157(6) | 2661(11) | 177(6) |
| C(20) | 8179(7) | −3162(5) | 2349(6) | 82(2) |

TABLE 8

Atomic coordinates (× 10⁴) and equivalent isotropic displacement
parameters (Å² '3 10³) for (THME)₂Sn₄(μ-OC₆H₃(CH₃)₂-2,6)₂.

|  | x | y | z | U (eq) |
|---|---|---|---|---|
| Sn(1) | 6711(1) | 2984(1) | 10085(1) | 23(1) |
| Sn(2) | 7978(1) | 2817(1) | 7777(1) | 26(1) |
| Sn(3) | 7012(1) | 5736(1) | 8690(1) | 27(1) |
| Sn(4) | 7675(1) | −44(1) | 9180(1) | 21(1) |
| O(1) | 7035(2) | 4286(4) | 7695(2) | 26(1) |
| O(2) | 6421(2) | 3688(4) | 9021(2) | 25(1) |
| O(3) | 7244(2) | 1275(4) | 8280(2) | 23(1) |
| O(4) | 7220(2) | 5225(4) | 9840(2) | 27(1) |
| O(5) | 7994(2) | 4497(4) | 8634(2) | 27(1) |
| O(6) | 7706(2) | 2143(3) | 9756(2) | 22(1) |
| O(7) | 6620(2) | 306(3) | 9653(2) | 23(1) |

TABLE 8-continued

Atomic coordinates (× 10⁴) and equivalent isotropic displacement
parameters (Å² '3 10³) for (THME)₂Sn₄(μ-OC₆H₃(CH₃)₂-2,6)₂.

|  | x | y | z | U (eq) |
|---|---|---|---|---|
| O(8) | 8580(2) | 1043(4) | 8551(2) | 25(1) |
| C(1) | 6411(3) | 3658(6) | 7383(3) | 31(1) |
| C(2) | 5883(3) | 3018(5) | 8575(2) | 26(1) |
| C(3) | 6590(3) | 929(5) | 7926(3) | 26(1) |
| C(4) | 6094(3) | 2366(5) | 7839(3) | 25(1) |
| C(5) | 5439(3) | 1761(6) | 7452(3) | 33(1) |
| C(6) | 7866(3) | 5557(6) | 10189(3) | 30(1) |
| C(7) | 8575(3) | 4842(6) | 9123(3) | 29(1) |
| C(8) | 8322(2) | 2795(5) | 10095(2) | 23(1) |
| C(9) | 8454(3) | 4537(5) | 9920(3) | 26(1) |
| C(10) | 9114(3) | 5015(6) | 10345(3) | 38(1) |
| C(11) | 6397(3) | −873(5) | 10097(3) | 24(1) |
| C(12) | 5791(3) | −1707(5) | 9886(3) | 27(1) |
| C(13) | 5556(3) | −2919(6) | 10326(3) | 40(2) |
| C(14) | 5910(3) | −3338(6) | 10970(3) | 42(2) |
| C(15) | 6495(3) | −2480(6) | 11181(3) | 37(1) |
| C(16) | 6751(3) | −1272(6) | 10757(3) | 28(1) |
| C(17) | 5375(3) | −1291(6) | 9202(3) | 38(1) |
| C(18) | 7406(3) | −453(6) | 11019(3) | 31(1) |
| C(19) | 9043(2) | −71(5) | 8339(2) | 21(1) |
| C(20) | 8859(3) | −1262(6) | 7826(3) | 28(1) |
| C(21) | 9361(3) | −2404(6) | 7661(3) | 40(1) |
| C(22) | 10012(3) | −2370(7) | 7962(3) | 44(2) |
| C(23) | 10196(3) | −1173(6) | 8450(3) | 39(1) |
| C(24) | 9721(3) | −24(6) | 8637(3) | 29(1) |
| C(25) | 8161(3) | −1376(6) | 7452(3) | 34(1) |
| C(26) | 9955(3) | 1293(6) | 9145(3) | 39(1) |

TABLE 9

Atomic coordinates (× 10⁴) and equivalent isotropic
displacement parameters (Å² × 10³) for (THME)₂Sn₃(μ-
OCH₂C(CH₃)₃)₂Ti(OCH₂C(CH₃)₃)₂.

|  | x | y | z | U (eq) |
|---|---|---|---|---|
| Sn(1) | 2674(1) | 6375(1) | −439(1) | 50(1) |
| Sn(2) | 1127(1) | 5165(1) | −299(1) | 50(1) |
| Sn(3) | 4042(1) | 5560(1) | 1810(1) | 65(1) |
| Ti(1) | 2499(2) | 4405(2) | 1886(2) | 49(1) |
| C(1) | 3621(10) | 4884(11) | −496(14) | 62(6) |
| C(2) | 2460(9) | 4062(8) | −431(14) | 45(5) |
| C(3) | 3820(10) | 3964(11) | 976(16) | 80(7) |
| C(4) | 3399(11) | 4145(11) | −207(15) | 58(5) |
| C(5) | 3639(10) | 3624(9) | −932(16) | 86(7) |
| C(6) | 1734(12) | 5432(12) | −2502(19) | 111(9) |
| C(7) | 1052(11) | 5748(9) | −3279(14) | 52(5) |
| C(8) | 1057(13) | 6529(14) | −3195(19) | 137(10) |
| C(9) | 288(13) | 5422(13) | −3252(15) | 150(12) |
| C(10) | 1119(13) | 5627(12) | −4400(15) | 133(11) |
| C(11) | 2087(11) | 2835(11) | 1932(18) | 110(9) |
| C(12) | 1193(12) | 2583(10) | 1524(16) | 65(6) |
| C(13) | 644(15) | 3084(11) | 1800(30) | 191(17) |
| C(14) | 1043(15) | 2581(18) | 300(20) | 218(19) |
| C(15) | 1070(11) | 1835(11) | 1850(20) | 148(12) |
| C(16) | 1252(11) | 5464(11) | 2144(16) | 77(6) |
| C(17) | 2652(11) | 5944(9) | 2769(15) | 66(6) |
| C(18) | 1623(10) | 6490(9) | 1175(14) | 58(5) |
| C(19) | 1748(12) | 6126(9) | 2250(16) | 55(5) |
| C(20) | 1501(12) | 6631(10) | 3006(16) | 95(7) |
| C(21) | 4153(13) | 7123(14) | 1210(20) | 125(10) |
| C(22) | 4112(12) | 7843(11) | 1589(18) | 64(6) |
| C(23) | 4080(20) | 7789(13) | 2710(30) | 184(15) |
| C(24) | 3268(17) | 8132(17) | 980(30) | 212(16) |
| C(25) | 4777(15) | 8291(14) | 1490(20) | 168(12) |
| C(26) | 2628(17) | 4190(18) | 4264(19) | 220(20) |
| C(27) | 3432(10) | 4072(10) | 5119(14) | 50(5) |
| C(28) | 3559(16) | 3363(12) | 5100(30) | 270(30) |
| C(29) | 3208(15) | 4301(17) | 6080(20) | 202(17) |
| C(30) | 4082(11) | 4578(11) | 4970(16) | 110(8) |
| O(1) | 3471(6) | 5459(6) | 98(9) | 53(3) |

TABLE 9-continued

Atomic coordinates (× $10^4$) and equivalent isotropic displacement parameters ($Å^2$ × $10^3$) for $(THME)_2Sn_3(\mu\text{-}OCH_2C(CH_3)_3)_2Ti(OCH_2C(CH_3)_3)_2$.

|       | x        | y        | z        | U (eq) |
|-------|----------|----------|----------|--------|
| O(2)  | 2170(5)  | 4522(5)  | 239(8)   | 42(3)  |
| O(3)  | 3616(6)  | 4401(6)  | 1728(9)  | 61(3)  |
| O(4)  | 1787(6)  | 5571(6)  | −1414(8) | 50(3)  |
| O(5)  | 2291(7)  | 3487(7)  | 1634(9)  | 64(4)  |
| O(6)  | 1434(6)  | 4914(6)  | 1517(9)  | 56(3)  |
| O(7)  | 2943(6)  | 5439(6)  | 2185(8)  | 45(3)  |
| O(8)  | 1793(6)  | 6112(5)  | 368(9)   | 48(3)  |
| O(9)  | 3520(6)  | 6615(5)  | 1251(8)  | 51(3)  |
| O(10) | 2606(8)  | 4335(6)  | 3278(9)  | 77(4)  |

TABLE 10

Atomic coordinates (× $10^4$) and equivalent isotropic displacement parameters ($Å^2$ × $10^3$) for $(THME)_2Sn_4(N(Si(CH_3)_3)_2)_2$.

|       | x         | y         | z        | U (eq) |
|-------|-----------|-----------|----------|--------|
| Sn(1) | 4706(1)   | 8893(1)   | 2841(1)  | 25(1)  |
| Sn(2) | −140(1)   | 8354(1)   | 2095(1)  | 25(1)  |
| Sn(3) | −499(1)   | 6326(1)   | 2077(1)  | 26(1)  |
| Sn(4) | 4022(1)   | 5528(1)   | 2846(1)  | 24(1)  |
| Si(1) | 3562(5)   | 10595(2)  | 2088(2)  | 30(1)  |
| Si(2) | 2448(4)   | 10175(2)  | 3789(2)  | 26(1)  |
| Si(3) | 2671(4)   | 4321(2)   | 1325(2)  | 26(1)  |
| Si(4) | 1290(4)   | 3977(2)   | 2980(2)  | 28(1)  |
| N(1)  | 3267(13)  | 9953(4)   | 2856(5)  | 24(2)  |
| N(2)  | 2297(13)  | 4590(4)   | 2337(5)  | 24(2)  |
| O(1)  | 2826(9)   | 8469(4)   | 1691(4)  | 22(2)  |
| O(2)  | 2270(9)   | 8350(4)   | 3302(4)  | 23(2)  |
| O(3)  | −255(9)   | 7348(4)   | 1328(4)  | 26(2)  |
| O(4)  | −892(10)  | 7345(4)   | 2767(4)  | 30(2)  |
| O(5)  | 2576(10)  | 6194(4)   | 1769(4)  | 24(2)  |
| O(6)  | 1664(10)  | 6095(4)   | 3289(4)  | 26(2)  |
| C(1)  | 3548(16)  | 8133(6)   | 1013(6)  | 28(3)  |
| C(2)  | 2919(14)  | 7392(6)   | 828(5)   | 19(2)  |
| C(3)  | 668(14)   | 7257(6)   | 603(5)   | 27(2)  |
| C(4)  | 3779(16)  | 6839(5)   | 1641(6)  | 25(2)  |
| C(5)  | 3748(19)  | 7026(6)   | 55(7)    | 45(3)  |
| C(6)  | 2981(16)  | 7659(6)   | 3750(6)  | 27(2)  |
| C(7)  | 1393(14)  | 7256(6)   | 4154(5)  | 23(2)  |
| C(8)  | −736(16)  | 7417(6)   | 3667(6)  | 35(3)  |
| C(9)  | 1804(17)  | 6392(6)   | 4141(6)  | 31(3)  |
| C(10) | 1495(17)  | 7494(6)   | 5077(6)  | 37(3)  |
| C(11) | 5398(19)  | 11364(7)  | 2463(7)  | 42(3)  |
| C(12) | 1110(20)  | 11034(8)  | 1619(8)  | 62(4)  |
| C(13) | 4530(20)  | 10110(7)  | 1212(8)  | 58(4)  |
| C(14) | 2683(18)  | 11213(6)  | 4060(7)  | 38(3)  |
| C(15) | 4001(17)  | 9671(6)   | 4720(7)  | 36(3)  |
| C(16) | −221(17)  | 9904(7)   | 3748(8)  | 38(3)  |
| C(17) | 4914(19)  | 4794(7)   | 1048(7)  | 40(3)  |
| C(18) | 470(20)   | 4561(7)   | 486(7)   | 52(3)  |
| C(19) | 3250(19)  | 3290(6)   | 1259(8)  | 45(3)  |
| O(20) | −840(20)  | 3396(8)   | 2406(8)  | 64(4)  |
| C(21) | 3202(18)  | 3316(7)   | 3549(8)  | 46(3)  |
| C(22) | 269(20)   | 4495(6)   | 3816(8)  | 46(4)  |

EXAMPLES

All compounds were synthesized under inert atmosphere conditions using standard glove-box techniques. All solvents were dried over Na°/benzophenone and stored over sieves immediately prior to use. THME-$H_3$ was used as received from Aldrich.

Example 1

Preparation of $(THME)_2Sn_3$

In a vial, $[Sn(N(CH_3)_2)_2]_2$ was dissolved in hexanes. Four-thirds of an equivalent of THME-$H_3$ were added and the reaction was stirred overnight. After warming slightly for 1 hour, the volatile material of the reaction was removed in vacuo. The final product was washed with hexanes to remove any residual starting materials. X-ray quality crystals were isolated from hot tetrahydrofuran (THF).

Example 2

Preparation of $(THME)_2Sn_4(\mu\text{-}OR)_2$

In a flask, $(THME)_2Sn_3$ was dissolved in THF. One equivalent of $Sn(OR)_2$, where OR=$OCH_2C(CH_3)_3$ and $\mu\text{-}OC_6H_3(CH_3)_2\text{-}2,6$, was added and the reaction stirred overnight. After warming slightly for 1 hour, the volatile material was removed in vacuo. The final product was washed with hexanes to remove residual starting materials. X-ray quality crystals were isolated from toluene.

Example 3

Preparation of $(THME)_2Sn_4(\mu\text{-}OR)_2Ti(OR)_2$

In a flask, $(THME)_2Sn_3$ was dissolved in THF. One equivalent of $Ti(OR)_4$, where OR=$OCH_2C(CH_3)_3$, was added and the reaction stirred overnight. After warming slightly for 1 hour, the volatile material was removed in vacuo. The final product was washed with hexanes to remove residual starting materials. X-ray quality crystals were isolated from toluene.

Example 4

Preparation of $(THME)_2Sn_4(N(Si(CH_3)_3)_2)_2$

In a flask, $Sn(N(Si(CH_3)_3)_2)_2$ was dissolved in THF. One half of an equivalent of THME-$H_3$ was added and the reaction stirred overnight. After heating to boil for 1 hour, the volatile material was removed in vacuo. The final product was washed with hexanes to remove residual starting materials. X-ray quality crystals were isolated from toluene.

The invention being thus described, it will be apparent to those skilled in the art that the same may be varied in many ways. Such variations are not to be regarded as a departure from the spirit and scope of the invention, and all such modifications are intended to be included within the scope of the following claims.

We claim:

1. The tin alkoxide compound comprising $(THME)_2Sn_3(M(L)_x)_y$, wherein THME is $(O-CH_2)_3C(CH_3)$, M is a metal atom selected from Sn and Ti, L is an organic/inorganic ligand selected from an alkoxide, a phenoxide and an amide, x is selected from 2 and 4 and y is selected from 0 and 1.

2. The tin alkoxide compound of claim 1 wherein L is an alkoxide selected from alkoxides with 1 to 5 carbon atoms.

3. The tin alkoxide compound of claim 2 wherein L is an alkoxide selected from methoxide, ethoxide, propoxide, iso-propoxide, butoxide, tert-butoxide, and neo-pentoxide.

4. The tin alkoxide compound of claim 1 wherein y is 0, wherein the compound is $(THME)_2Sn_3$.

5. The tin alkoxide compound of claim 1 wherein M is Sn, y is 1, x is 2, and L is $\mu\text{-}OCH_2C(CH_3)_3$, wherein the compound is $(THME)_2Sn_4(\mu\text{-}OCH_2C(CH_3)_3)_2$.

6. The tin alkoxide compound of claim 1 wherein M is Sn, y is 1, x is 2, and L is $\mu OC_6H_3(CH_3)_2\text{-}2,6$, wherein the compound is $(THME)_2Sn_4(\mu\text{-}OC_6H_3(CH_3)_2\text{-}2,6)_2$.

7. The tin alkoxide compound of claim 1 wherein M is Ti, y is 1, x is 4, and L is $OCH_2C(CH_3)_3$, wherein the compound is $(THME)_2Sn_3Ti(OCH_2C(CH_3)_3)_4$.

8. The tin alkoxide compound of claim 1 wherein M is Sn, y is 1, x is 2, and L is $N(Si(CH_3)_3)_2$, wherein the compound is $(THME)_2Sn_4(N(Si(CH_3)_3)_2)_2$.

9. The tin alkoxide compound of claim 1 wherein the tin alkoxide compound at least one accessible electron pair.

10. A method of making a tin alkoxide compound $(THME)_2Sn_3$ comprising, mixing in a non-reactive solvent, $(HO-CH_2)_3C(CH_3)$ with a tin compound selected from $Sn(N(CH_3)_2)_2$ and $Sn(N(Si(CH_3)_3)_2)_2$.

11. The method of claim 10 wherein the non-reactive solvent is selected from hexanes, toluene, tetrahydrofuran (THF), and pyridine.

12. A method of making a tin alkoxide compound $(THME)_2Sn_4(\mu\text{-}OR)_2$ comprising, mixing in a non-reactive solvent $(THME)_2Sn_3$ and $Sn(OR)_2$ wherein OR is selected from $OCH_2C(CH_3)_3$ and $\mu\text{-}OC_6H_3(CH_3)_2\text{-}2,6$.

13. A method of making a tin alkoxide compound $(THME)_2Sn_3Ti(OCH_2C(CH_3)_3)_4$ comprising, mixing in a non-reactive solvent $(THME)2Sn_3$ and $Ti(OR)_4$ wherein OR is selected from $OCH_2C(CH_3)_3$.

14. A method of making a tin alkoxide compound $(THME)_2Sn_4(N(Si(CH_3)_3)_2)_2$ comprising, mixing in a non-reactive solvent $(HO-CH_2)_3C(CH_3)$ and $Sn(N(Si(CH_3)_3)_2)_2$.

\* \* \* \* \*